United States Patent
Nüesch

[11] Patent Number: 6,110,141
[45] Date of Patent: Aug. 29, 2000

[54] BREAST PUMP AND OVERFLOW PROTECTION FOR AN APPARATUS FOR SUCKING A BODY FLUID OFF

[75] Inventor: Hansueli Nüesch, Remetschwil, Switzerland

[73] Assignee: Nüesch Logistik, Zuzwil, Switzerland

[21] Appl. No.: 09/181,392

[22] Filed: Oct. 28, 1998

[30] Foreign Application Priority Data

Oct. 30, 1997 [DE] Germany .............................. 197 47 842

[51] Int. Cl.$^7$ ...................................................... A61M 1/06
[52] U.S. Cl. ............................................... 604/74; 604/30
[58] Field of Search .................................. 604/30, 32, 73, 604/74, 246; 251/335.2; 417/309, 566, 298

[56] References Cited

U.S. PATENT DOCUMENTS 5,071,403  12/1991  Larsson .

*Primary Examiner*—Wynn Wood Coggins
*Assistant Examiner*—Kevin C. Sirmons
*Attorney, Agent, or Firm*—Martin A. Farber

[57] ABSTRACT

A breast pump for pumping milk from a woman's breast comprises a breast hood to be applied onto the woman's breast. A suction chamber communicates with said breast hood, and a suction pump communicates with the suction chamber. A milk collecting vessel or other space receives the milk that is pumped from the woman's breast. Between said suction chamber and the milk collecting means is a check valve. In communication with the suction chamber and the suction pump is an overflow protection for protecting the suction pump from being flooded by an excess of milk. The overflow protection comprises an valve housing elongated along a longitudinal axis. The housing has two opposing end walls, a first one of which including an entrance opening nearer to the suction chamber, the second end wall defining an outlet opening nearer to the suction pump. Within the valve housing is an elongated valve body movable along the longitudinal axis of the housing and is provided with an impact surface opposite the entrance opening. The impact surface extends substantially transversely to the direction of entrance flow through the entrance opening so that is impacted by any milk on the way to flood the suction pump. A shutter surface of the valve body is arranged in the region of the outlet opening in order to be able to obturate it. The overflow protection has an elongated by-passing space which extends from the region of the entrance opening to the outlet opening and communicates with them, thus by-passing the valve body over an elongated pathway as long as the latter is not impacted by milk and does not obturate the outlet opening.

29 Claims, 3 Drawing Sheets

BREAST PUMP AND OVERFLOW PROTECTION FOR AN APPARATUS FOR SUCKING A BODY FLUID OFF

FIELD OF THE INVENTION

The present invention, in a first aspect, relates to a breast pump for pumping milk from a woman's breast which comprises a breast hood to be applied onto the woman's breast, and a suction chamber communicating with said breast hood. A suction pump communicates with the suction chamber to which adjoins a milk collecting space for receiving milk pumped from said woman's breast. Suction chamber and milk collecting space are separated by a check valve. It is known to provide an overflow protection which communicates with the suction chamber and the suction pump to avoid that the latter is flooded by milk. The present invention, in a second aspect, relates to an overflow protection for any apparatus for sucking a body fluid off including scavenger fluids introduced into the body, but also sputum, secretion fluids (e.g. in the lungs), pus, blood, etc. that should not reach the pump.

BACKGROUND OF THE INVENTION

U.S. Pat. No. 5,071,403 discloses an overflow protection which consists of an air permeable filter interposed in the suction pathway between the breast hood and the pump. This filter is, however, substantially impermeable by milk. If milk reaches the filter, e.g. due to the fact that the collecting space is already completely filled with milk, the pores of the filter material are becoming closed when milk wets it. The disadvantage of this approach is that the filter, after contacting milk, can, in general, no longer be used and, therefore, has to be replaced. Moreover the filter constitutes a not inconsiderable resistance against suction air flow resulting in the necessity of stronger dimensioning the pump and in a higher energy consumption. Just the latter is undesirable when used in battery operated pumping appliances.

Clearly, many check valves, mostly of the ball type, are known in the art and could be used as a protection against some entering liquid. However, there is a certain time gap from the moment when the liquid enters the valve housing up to full closure of the valve. In most applications, this does not do any harm. However, when milk enters a space where it can hardly be removed, it would form a nutritive agent for bacteria which, just in an application for the human body and, above all, in breast pumps, should be avoided by all means.

SUMMARY OF THE INVENTION

Therefore, an object of the present invention is to conceive a breast pump in which the pump unit is protected against any contact with milk even when the collecting space or vessel is filled up completely, but avoiding to provide relative high energy consumption.

This object is achieved according to the present invention by an overflow protection which comprises a valve housing elongated along a longitudinal axis and having two opposing end walls. A first end wall includes an entrance opening nearer to the suction chamber and, thus, defining a direction of entrance flow. The second end wall defines an outlet opening nearer to the suction pump. Within the valve housing, an elongated valve body is movable along its longitudinal axis. This elongated valve body has a predetermined volume and an impact surface opposite the entrance opening. The impact surface extends substantially transversely to the direction of entrance flow so as it is directly and fully impacted by milk on the way to flood said suction pump not allowing any ineffective deviation. In the region of the outlet opening of the valve housing, the elongated valve body has a shutter surface in order to be able to obturate this opening. An elongated by-passing space or channel extends from a region of the entrance opening to the outlet opening and communicates with both openings, thus by-passing the valve body as long as the latter is not impacted by milk and does not obturate the outlet opening.

The ball check valves, due to their ball configuration which forms a streamlined body, deviate entering liquid easily to the side to reach the valve's outlet. On the other hand, the pathway from one face of a ball to the opposite one is relative short. Therefore, by providing an elongated valve body that can only be by-passed by an elongate by-passing space or channel a period of response long enough to ensure that no milk exits the outlet opening towards the pump where it could not be removed and would spoil the whole appliance. The fact that this elongated valve body has an impact surface which extends substantially transversely to the direction of entrance flow no easy deviation of liquid is enhanced. "Substantially transversely" should mean, in the context of this description, that it does not provide a streamlined outer surface to deviate the entering liquid easily towards the outlet opening. Moreover, the fact that sucked air has no longer to pass micro-pores of a filter, but can stream freely through the by-passing space reduces the pressure losses considerably and, thus, enables the use of smaller pumps consuming less power.

If, according to a preferred embodiment, the longitudinal axis of the housing and the valve body extends at least partially in vertical direction, the outlet opening being above the entrance opening, two effects are attained: First, any milk which enters the by-passing channel has the opportunity to drain off easily. Second, gravity will form or at least contribute to a return force acting onto the valve body to render the outlet opening open immediately after the liquid's impact does no longer act onto the impact surface. This means that instead of having to exchange the overflow protection whenever reached by liquid, as it was the case with the above-mentioned filter, the overflow protection is operative again as soon as the milk or other fluid has ceased to apply pressure on the impact surface.

More preferred, however, is an embodiment where an elastic membrane is used to interconnect the valve body and the housing. Its elasticity will at least contribute to a restoring force, even if a breast pump (or other pump for removing a fluid out of the body) is held so that the longitudinal axis of the overflow protection is no longer vertical, or if it cannot be arranged in a vertical direction for some constructive reasons. Moreover, although it is preferred to form the valve body as a float member being lighter in weight than a volume of milk which corresponds to said predetermined volume, the use of an elastic membrane is of special value, because it helps in orienting the floating body, which may have a tendency to tilt to the side under some circumstances and to jam on the walls of the housing, along the longitudinal axis.

BRIEF DESCRIPTION OF THE DRAWINGS

Further details will become apparent from the following description of a preferred embodiment represented in the drawings in which.

DETAILED DESCRIPTION OF THE DRAWINGS

Figure 1:
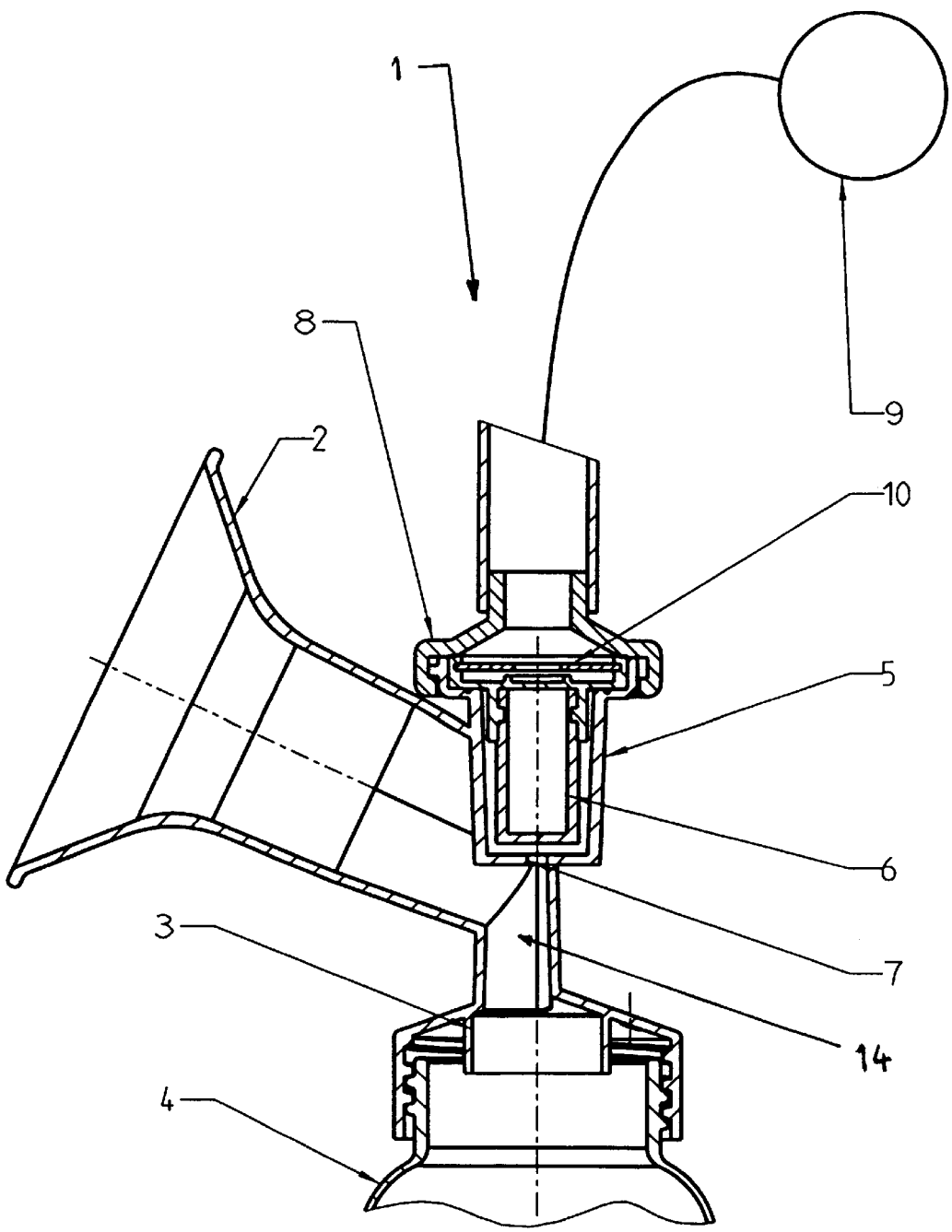
FIG. 1 is a vertical cross-section through a breast pump comprising a breast hood, a valve arrangement and a collecting vessel only shown in part and being mounted in a connection area.

FIG. 1 shows a breast pump 1 comprising a breast hood 2, a connection area including a check valve 3 of the flap type which area comprises a thread for screwing a collecting receptacle 4 on it. The check valve 3 separates the collecting receptacle 4 below from an upper suction chamber which communicates with an elongated valve housing 5 for overflow protection in which an elongated main body 6 of the valve is axially and vertically moveable. Although the valve housing 5 is shown integral with the breast hood 2 and the remaining parts of breast pump 1, it may suitably be detachably mounted so as to be able to replace or to clean it. In this way, it can form a separate spare part.

The interior of the valve housing 5 has a lower end wall 5a (FIG. 2) which includes an entrance opening 7. As shown, the entrance opening 7 is aligned with a longitudinal axis 11, shown in dash-dotted lines, of the housing 5 and the main body 6. In this way, the entrance opening 7 provides communication to the breast hood 2 via the suction chamber below the valve housing 5 and a connecting channel not referenced.

On top, the valve housing 5 is provided with a suction connection piece 8 (FIG. 1) to communicate with a suction pump 9 via an outlet opening 10. In order to prevent that milk may be sucked into the pump 9, especially when the collecting receptacle 4 is completely filled up, the main body 6 is moveable in upward direction by the pressure of any liquid (milk) that may enter through the entrance opening, thereby impacting an impact surface 6a of the main body 6 which extends transversely to the direction of flow (direction of the dash-dotted longitudinal axis) defined by the entrance opening 7. By such an impact or pressure of the liquid, the valve body moves towards the outlet opening 10 formed in another end wall 5b opposite the end wall 5a of the valve housing 5. Thus, the outlet opening 10 will be obturated by the valve body as explained below.

Figure 2:
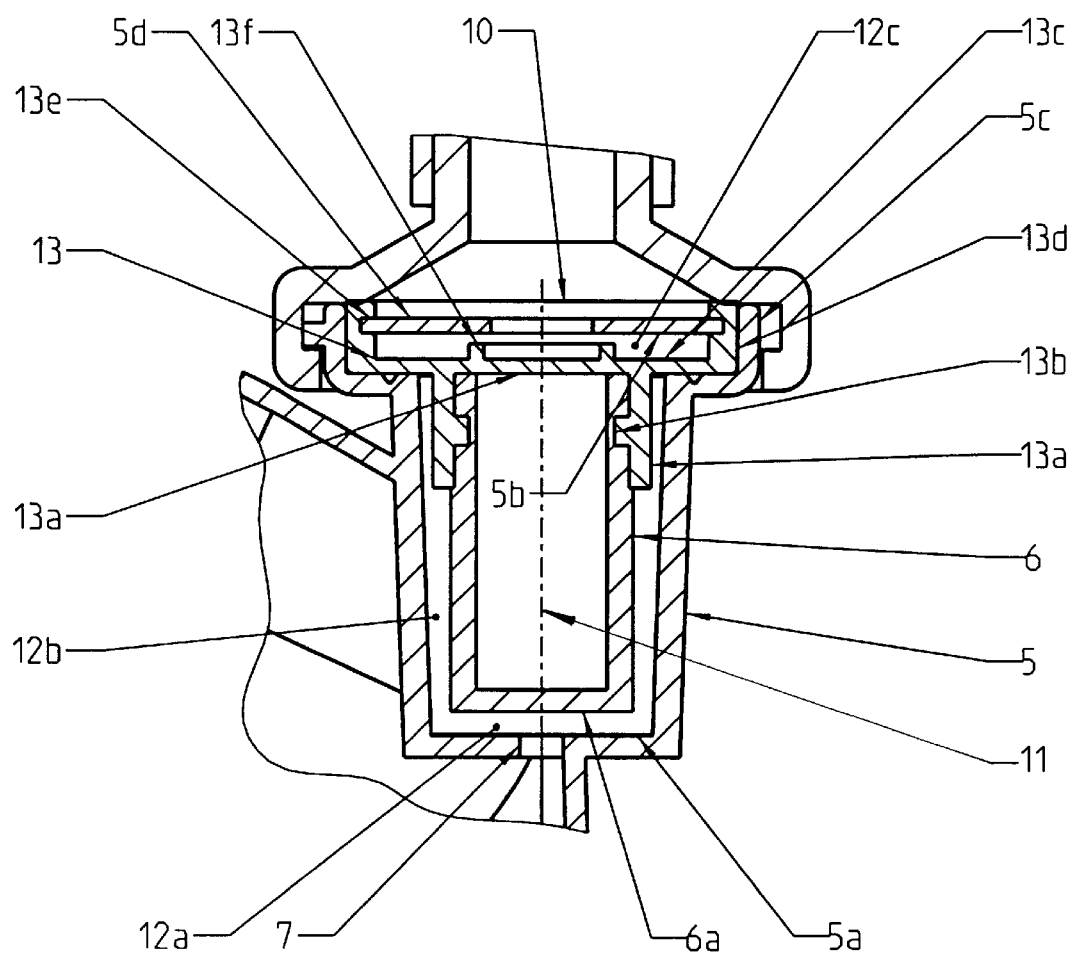
FIG. 2 is a vertical cross-section through a valve housing and a valve body.

As best seen in FIG. 2, the valve housing 5 and the main body 6 is each formed as a cylindrical sleeve along the common longitudinal axis 11. Departing from the entrance opening 7, a first portion 12a of a by-passing channel 12a, 12b, 12c extends between the lower or first end wall 5a of the housing 5 and the impact surface 6a of the main body 6 towards an annular, axially extending space 12b between the peripheral surface of the main body 6 and the inner wall surface of the housing 5. The valve body is formed both by the main body 6 and an elastic membrane element 13 (shutter surface) which, in particular, is formed of silicone rubber. This membrane element 13 connects the moveable main body 6 with the valve housing 5. To this end, the membrane element 13 possesses preferably a central connecting and holding portion 13a to which the main body is connected suitably within the region of its upper end. Preferably, the central connecting and holding portion 13a is formed in a way so as to close the upper end of the main body (thus forming part of the whole valve body), on the one hand, and to surround its upper peripheral surface by a substantially cylindrical portion. An inner projection or bulge 13b, which protrudes towards the longitudinal axis 11, engages a corresponding groove of the main body 6. It is clear, however, that the arrangement could be reversed by providing the holding portion 13a with a groove and the main body 6 with a corresponding annular flange. However, within the scope of the present invention any connection could be used, such as an adhesive.

Figure 3:
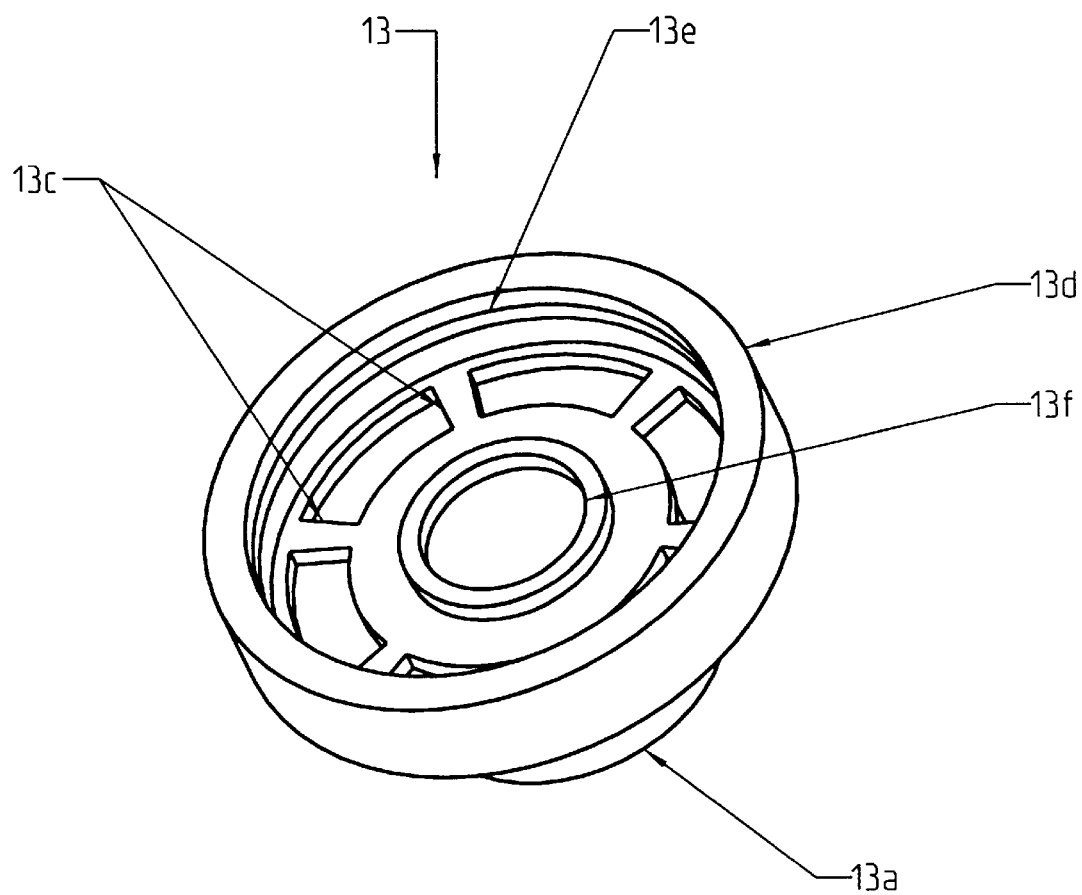
FIG. 3 is a perspective view of a membrane element.

As may be seen from FIGS. 2 and 3, elastic webs 13c of the membrane element 13 (shutter surface) extend radially outside, thus connecting the holding portion 13a to a radial outer flange portion 13d extending peripherally around the longitudinal axis 11. In accordance with FIG. 2, forms another holding structure for holding the second end wall 5d in spaced relationship. To this end, the valve housing 5 forms a somewhat enlarged receiving portion 5c for receiving the radial outer flange portion 13d of the membrane element 13. Now, when the suction connection piece 8 (FIG. 1) is screwed onto the receiving portion 5c through an outer thread of the same, the flange portion 13d of the membrane element 13 is clamped within the receiving portion 5c.

The by-passing channel portions 12a, 12b between the main body 6 and the valve housing 5 lead to through holes defined by the webs 13c and extending in-between the same which, in this way, form part of the by-passing space and lead to another substantially horizontal portion 12c of the by-passing channel 12a, 12b, 12c. In order to ensure a defined minimum space 12c, the holding portion 13d fixes the relative stiff disk-like end wall 5d of the valve housing 5 in spaced relationship, preferably by inserting it into an annular groove 13e of the elastic membrane element 13. This end wall, as well as the whole valve housing, is preferably made from plastic material. The end wall 5d comprises a, preferably central, outlet opening 10. Furthermore, it is convenient, if an axially protruding annular projection 13f of the elastic membrane element 13 extends toward an ring-like area of the end wall 5d around the outlet opening 10. This elastic projection 13f, particularly consisting of silicone rubber, ensures tight obturation of the area around the outlet opening 10, on the one hand, and a certain minimum space 12c, on the other hand.

In operation of a breast pump, when the milk level rising above the collection receptacle reaches the entrance opening 7, a jet of milk impinges onto the impact surface 6a of the valve body 6. The valve body 6 is then moved upwards and towards the outlet opening 10 thereby elongating the webs 13c due to its impact force. During this time of upward movement, the milk may fill the by-passing channel portions 12a, 12b and even 12c, but has not time enough to reach the outlet opening 10 before it is obturated by the annular projection 13f of the membrane element 13. For the by-passing portion 12c is narrowing in the region between the outlet opening 10 and the projection 13f of the membrane element which enhances a suction effect onto the membrane 13, thus closing the opening 10. Even if the impact force and the suction effect is insufficient to close the outlet opening immediately, the milk having entered the by-passing channel portions 12a, 12b causes an increased suction resistance that acts onto the membrane element 13 in upward direction. The fact that, in the preferred embodiment, the main body 6 is made hollow (or of a light material) so that its volume is lighter in weight than an equal volume of milk, it forms a floating body, the buoyancy of which ensures obturating the outlet opening 10 even under unfavorable circumstances.

In breast pump systems where two breast hoods are used, it is preferred to assign an overflow protection and overflow valve to each breast hood, although it would, alternatively, be possible to employ a single overflow protection arranged in a conduit common to both breast hoods.

From the above description, it will be seen that the overflow protection according to the present invention could also be applied in medical pumping systems for sucking other liquids off the human body, as mentioned at the outset.

What is claimed is:

1. A breast pump for pumping milk from a woman's breast, comprising:
   a breast hood for applying onto said woman's breast;
   a suction chamber communicating with said breast hood;
   suction pump means communicating with said suction chamber;
   milk collecting means for receiving milk pumped from said woman's breast;
   a check valve between said suction chamber and said milk collecting means; and
   overflow protection means communicating with said suction chamber and said suction pump means, protecting said suction pump means from being flooded by said milk;
   wherein said overflow protection means comprises:
   wall means forming a valve housing being elongated along a longitudinal axis and having two opposing end walls, a first one of which includes an entrance opening nearer to said suction chamber and, thus, defining a direction of entrance flow, a second one of said end walls defining an outlet opening nearer to said suction pump,
   an elongated valve body movable within said valve housing along said longitudinal axis, said elongated valve body having a predetermined volume and being provided with an impact surface opposite said entrance opening and extending substantially transversely to said direction of entrance flow so as to be impacted by milk on the way to flood said suction pump, and a shutter surface in a region of said outlet opening in order to be able to obturate the latter, and
   elongated by-passing means extending from a region of said entrance opening to said outlet opening and communicating with both said entrance opening and said outlet opening, thus by-passing said valve body as long as the latter is not impacted by milk and does not obturate said outlet opening.

2. A breast pump as claimed in claim 1, wherein said valve body comprises a main body and elastic membrane means including an inner region and an outer region, said inner region being connected to said elongated valve body, said outer region being connected to said wall means so as to maintain said main body in a predetermined position relative to said wall means, said membrane means having a through hole arrangement forming part of said by-passing means.

3. A breast pump as claimed in claim 2, wherein said second end wall engages said membrane means so that said second end wall and said membrane means are held in a fixed position relative to each other.

4. A breast pump as claimed in claim 3, wherein said membrane means comprise a first holding structure for holding said second end wall in spaced relationship.

5. A breast pump as claimed in claim 4, wherein said first holding structure of said membrane means comprises annular groove means for receiving an edge region of said second wall means.

6. A breast pump as claimed in claim 5, wherein said annular groove is open towards said longitudinal axis to receive said second end wall.

7. A breast pump as claimed in claim 4, wherein said first holding structure of said membrane means comprises annular flange means overlapping and holding said second end wall.

8. A breast pump as claimed in claim 2, wherein said membrane means comprise a second holding structure for mounting and holding said main body.

9. A breast pump as claimed in claim 8, wherein said second holding structure comprises at least one pair of an interengaging indentation and protrusion.

10. A breast pump as claimed in claim 9, wherein at least one of said interengaging indentation and protrusion is annular and surrounds the periphery of said main body.

11. Overflow protection as claimed in claim 2, wherein said membrane means comprise a second holding structure for mounting and holding said main body.

12. Overflow protection as claimed in claim 11, wherein said second holding structure comprises at least one pair of an interengaging indentation and protrusion.

13. Overflow protection as claimed in claim 12, wherein at least one of said interengaging indentation and protrusion is annular and surrounds the periphery of said main body.

14. A breast pump as claimed in claim 2, wherein said elongated valve body is maintained in a non-obturating position relative to said outlet opening by said membrane means the elasticity of which providing a return bias when obturating said outlet opening.

15. A breast pump as claimed in claim 2, wherein said through hole arrangement comprises at lest two through holes defined by radially extending webs of said membrane means.

16. A breast pump as claimed in claim 2, wherein said membrane means comprise an annular projection protruding against a surface of said second end wall surrounding said outlet opening.

17. A breast pump as claimed in claim 1, wherein said longitudinal axis extends at least partially in vertical direction, the outlet opening being above said entrance opening.

18. A breast pump as claimed in claim 1, wherein said elongated valve body is formed as a float valve member being lighter in weight than a volume of milk which corresponds to said predetermined volume.

19. An overflow protection for an apparatus for sucking a body fluid off by means of a suction pump sucking said body fluid over a predetermined pathway including a suction chamber and to enter a fluid collector space, wherein said overflow protection is to be interposed between said pathway and said suction pump and comprises
   wall means forming an valve housing being elongated along a longitudinal axis and having two opposing end walls, a first one of which including an entrance opening nearer to said suction chamber and, thus, defining a direction of entrance flow, a second one of said end walls defining an outlet opening nearer to said suction pump,
   an elongated valve body movable within said valve housing along said longitudinal axis, said elongated valve body having a predetermined volume and being provided with an impact surface opposite said entrance opening and extending substantially transversely to said direction of entrance flow so as to be impacted by milk on the way to flood said suction pump, and a shutter surface in a region of said outlet opening in order to be able to obturate the latter, and
   elongated by-passing means extending from a region of said entrance opening to said outlet opening and communicating with both said entrance opening and said outlet opening, thus by-passing said valve body as long as the latter is not impacted by milk and does not obturate said outlet opening.

20. Overflow protection as claimed in claim 19, further comprising elastic membrane means comprising an inner region and an outer region, said inner region being connected to said elongated valve body, said outer region being connected to said wall means so as to maintain said valve body in a predetermined position relative to said wall means, said membrane means having at least one through hole forming part of said by-passing means.

21. Overflow protection as claimed in claim 20, wherein said second end wall engages said membrane means so that said second end wall and said membrane means are held in a fixed position relative to each other.

22. Overflow protection as claimed in claim 21, wherein said membrane means comprise a first holding structure for holding said second end wall in spaced relationship.

23. Overflow protection as claimed in claim 22, wherein said first holding structure of said membrane means comprises annular groove means for receiving an edge region of said second wall means.

24. Overflow protection as claimed in claim 23, wherein said annular groove is open towards said longitudinal axis to receive said second end wall.

25. Overflow protection as claimed in claim 22, wherein said first holding structure of said membrane means comprises annular flange means overlapping and holding said second end wall.

26. Overflow protection as claimed in claim 20, wherein said elongated valve body is maintained in a non-obturating position relative to said outlet opening by said membrane means the elasticity of which providing a return bias when obturating said outlet opening.

27. Overflow protection as claimed in claim 20, wherein said membrane means comprise an annular axial projection protruding against a surface of said second end wall surrounding said outlet opening.

28. Overflow protection as claimed in claim 19, wherein said elongated valve body is formed as a float valve member being lighter in weight than a volume of milk which corresponds to said predetermined volume.

29. Overflow protection as claimed in claim 19, wherein said through hole arrangement comprises at least two through holes defined by radially extending webs of said membrane means.

* * * * *